United States Patent [19]

Columbus

[11] 4,439,526

[45] Mar. 27, 1984

[54] CLUSTERED INGRESS APERTURES FOR CAPILLARY TRANSPORT DEVICES AND METHOD OF USE

[75] Inventor: Richard L. Columbus, Rochester, N.Y.

[73] Assignee: Eastman Kodak Company, Rochester, N.Y.

[21] Appl. No.: 401,753

[22] Filed: Jul. 26, 1982

[51] Int. Cl.³ .................... G01N 27/28; G01N 1/00
[52] U.S. Cl. ............................ 436/180; 73/864.91; 204/409; 422/100
[58] Field of Search .............. 422/55, 58, 100, 102; 356/246; 204/409, 416; 73/864.91; 436/180, 174

[56] References Cited

U.S. PATENT DOCUMENTS 4,233,029 11/1980 Columbus .................. 422/100 X
4,323,536 4/1982 Columbus .................. 422/100 X

FOREIGN PATENT DOCUMENTS 10456 4/1980 European Pat. Off. .

Primary Examiner—Arnold Turk
Attorney, Agent, or Firm—Dana M. Schmidt

[57] ABSTRACT

Device and method for transporting liquid within a passage, the device having improved acess means for conveying liquid into the passage. Each access means comprises at least two and preferably more than two, apertures, one larger than the others, the apertures being sized so that only the larger aperture permits independent initiation of flow within the passage.

7 Claims, 6 Drawing Figures (COMPARATIVE EXAMPLE)

(COMPARATIVE EXAMPLE)

(COMPARATIVE EXAMPLE)

CLUSTERED INGRESS APERTURES FOR CAPILLARY TRANSPORT DEVICES AND METHOD OF USE

FIELD OF THE INVENTION

This invention is directed to devices and a method for the capillary transport of liquid along a passage within the device, and specifically to means in the device for conveying liquid into such passage.

BACKGROUND OF THE INVENTION

As described in European Patent application No. 0,010,456, published April 3, 1980, flow-through apertures providing liquid access to a capillary zone or passage are difficult to use if they are circular in shape. The difficulty concerns the tendency of the liquid to not enter the aperture. The smooth cylindrical sidewalls of circular apertures tend to cause a drop of the liquid deposited in the vicinity of the aperture to draw away from the aperture, rather than enter it, unless careful centering is achieved. If careful centering does not occur, the drop circumference does not completely encompass the aperture, but instead intersects it. The surface tension of the liquid in such cases tends to push the liquid away from such circular aperture instead of into it.

The device described in the aforesaid European Application eliminates the problem by the use of special aperture sidewall configurations. These configurations have been found to be very effective and useful in urging the drop to enter the aperture. However, such configurations exclude circular apertures formed by cylindrical sidewalls. Because circular apertures are the simplest to manufacture, it would also be useful to provide a device which allows circular flow-through or ingress apertures to be used even when metering errors occur. However, as noted above, this requires that the drop always encompass the circular aperture.

It will be appreciated that the metering displacement error, that is, the distance between the aperture center and the center of the deposited quantity of liquid, is an important part of the problem. It is impractical to reduce that error to zero by means of metering apparatus and aperture location tolerance control. The only other readily manipulatable variables are the quantity of deposited liquid and the size of the ingress aperture. The quantity of deposited liquid could be increased to insure that the aperture is always encompassed by the circumference of the deposited liquid, as determined by the maximum expected displacement error. However, due to the magnitude of such maximum displacement error such an approach could drastically and unacceptably increase the requisite volume of deposited liquid from the presently preferred level of about 10 $\mu$l.

The opposite approach would be to hold the deposited liquid volume constant and reduce the aperture size. This could insure that the aperture is encompassed by the deposited liquid, even when maximum displacement errors occur. However, apertures significantly smaller than about 3 mm diameter have several drawbacks. The surface area contacted by the drop becomes so large, compared to the area of the aperture, that residual liquid tends to remain on the exterior around the aperture, rather than drain into the aperture. Such behavior alters the volume of the liquid that passes through the capillary passage, which in turn can produce errors in the detected analyte levels if such is the end use of the passage. In addition, the large surface contact area that is contacted (compared to the area of the aperture) tends to induce the drop to wander away from a position centered on the aperture.

Thus, for use of circular ingress apertures, a dilemma has existed prior to this invention. Neither increasing the quantity of liquid relative to a fixed size of ingress aperture, nor decreasing the aperture size relative to a fixed quantity of deposited liquid, has appeared to be a satisfactory solution to the reliable use of circular ingress apertures for liquid deposited with a potential displacement error.

(Merely increasing the size of the aperture to encompass the displacement error is not a satisfactory solution because the drop could enter the aperture without contacting the upper surface of the transport passage. In such a case, capillary flow would not initiate.)

SUMMARY OF THE INVENTION

I have discovered a solution to the aforementioned dilemma, namely, a first access aperture capable of having flow-through dimensions small enough to be reliably encompassed by practical drop sizes with practical displacement errors, which, when used with an additional aperture disposed close to the first aperture, provides superior transfer of liquid from the exterior surface to the transport passage.

More specifically, in accord with one aspect of the invention, there is provided a liquid transport device having an exterior surface for receipt of liquid deposited, and wall means interior of the surface for transporting liquid by capillary attraction along a passage. Access means are also provided, for fluidly connecting the exterior surface and a portion of the passage so that liquid deposited on the exterior surface at the access means is transported into and along the passage. The device is improved in that the access means comprises a cluster of apertures extending from the exterior surface to the passage, one of the apertures having a maximum flow-through dimension that allows the liquid to independently initiate capillary flow along the passage. The other apertures have smaller maximum flow-through dimensions that allow liquid to form menisci along the passage wall but prevent independent initiation of capillary flow along the passage.

A method is also provided for improving the flow of deposited liquid from an exterior deposit surface of a transport device to an interior transport passage, the surface including a cluster of apertures extending to the passage, only one of which has a maximum flow-through dimension that is sufficiently large as to allow the liquid to independently initiate transport in the passage. The method comprises the steps of (a) positioning such transport device with the one larger aperture located within a predetermined error range measured from a desired metering position, and (b) depositing such liquid onto the surface so as to encompass the one larger aperture and at least one other aperture.

Thus, it is an advantage of the present invention that the ingress aperture can be circular in flowthrough shape, and still insure proper wetting of the interior capillary passage.

It is a related advantage of the invention that the size of the ingress aperture is reduced to insure it is encompassed within a quantity of deposited liquid, and still provide satisfactory liquid flow into the passage.

Another related advantage of the invention is that such ingress apertures provide more complete drainage into the passage, so that minimal residual liquid is left on the exterior surface.

Still another advantage of the invention, and one that is applicable whether the invention is applied to solve a displacement error problem or not, is that the additional, smaller apertures that deliver menisci along the passage wall as described above, act to slow down the rate of transport of liquid within the passage.

Other advantages and features will become apparent upon reference to the following "Description of the Preferred Embodiments", when read in light of the attached drawings.

DESCRIPTION OF THE PREFERRED EMBODIMENTS

Figure 1:
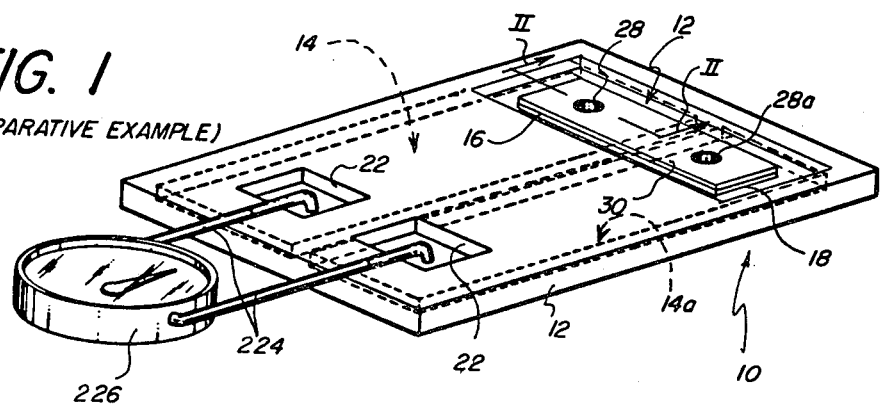
FIG. 1 is an isometric view of an ISE test element, illustrating the problem solved by the invention.
Figure 2:
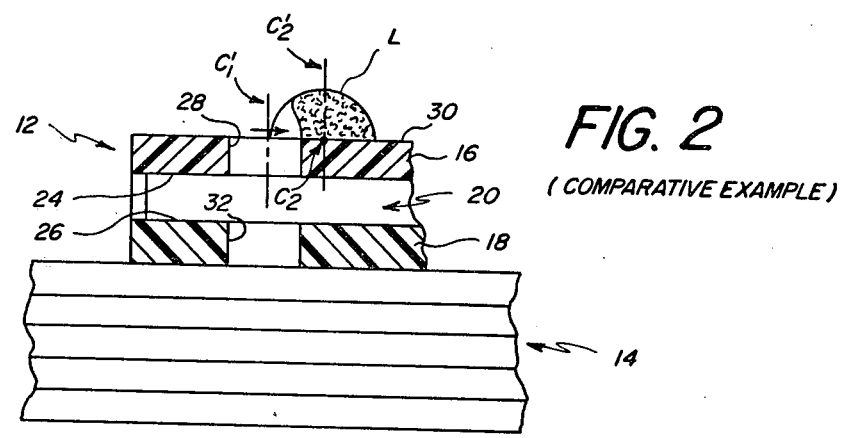
FIG. 2 is a fragmentary vertical section view of the liquid access aperture of FIG. 1, further illustrating the problem solved by the invention.

The problem to which the invention is addressed is illustrated in FIGS. 1 and 2. Device 10 comprises a potentiometric test element as described in U.S. Pat. No. 4,233,029. Ion bridge 12 is disposed above two ion-selective electrodes (ISE's) 14 and 14a. The bridge comprises two members 16 and 18 spaced apart a distance effective to form a capillary transport passage 20 between opposing surfaces 24 and 26, FIG. 2. Useful values for such spacing distance range between about 50 microns and about 600 microns. Access or ingress apertures 28 and 28a are formed in member 16, FIG. 1, connecting exterior surface 30 of member 16 with passage 20. Each aperture 28 and 28a is disposed to receive a separate drop. Apertures 32 are formed in member 18, extending to ISE's 14 and 14a, and are preferably aligned with apertures 28 and 28a, respectively, as indicated in FIG. 2.

Apertures 28 and 28a are adjusted in size and flow-through volume so that the volume of liquid deposit L that flows through the aperture will adequately wet passage 20 and initiate capillary flow, as is further described in the aforesaid U.S. patent.

When aperture 28 is generally circular, and the center $C_2$ on center line $C'_2$ of quantity L is displaced from center line $C'_1$ of aperture 28 so that the circumference of the deposit L intersects, rather than encompasses, the circumference of aperture 28, liquid deposited as a quantity L experiences a tendency to sit up on surface 30, FIG. 2, rather than enter aperture 28. Under these conditions, the meniscus of quantity L apparently encounters an energy barrier that displaces the meniscus away from the aperture, as shown by the arrow. The liquid thus is prevented from entering the aperture, and flow is not initiated.

Figure 3:
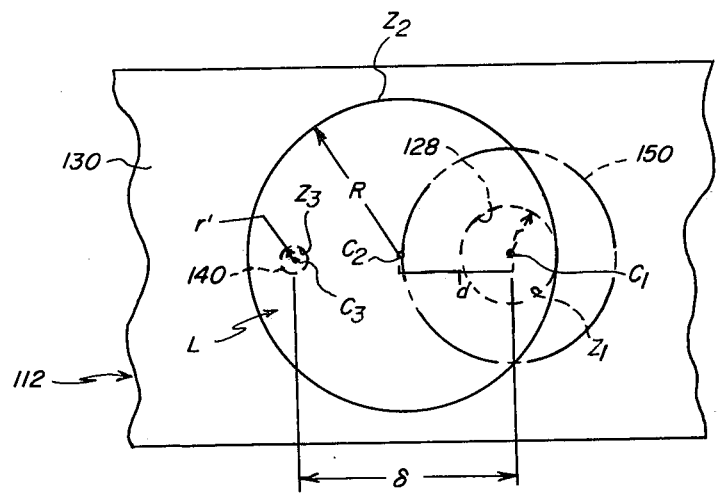
FIG. 3 is a fragmentary plan view of a device constructed in accordance with the invention.
Figure 4:
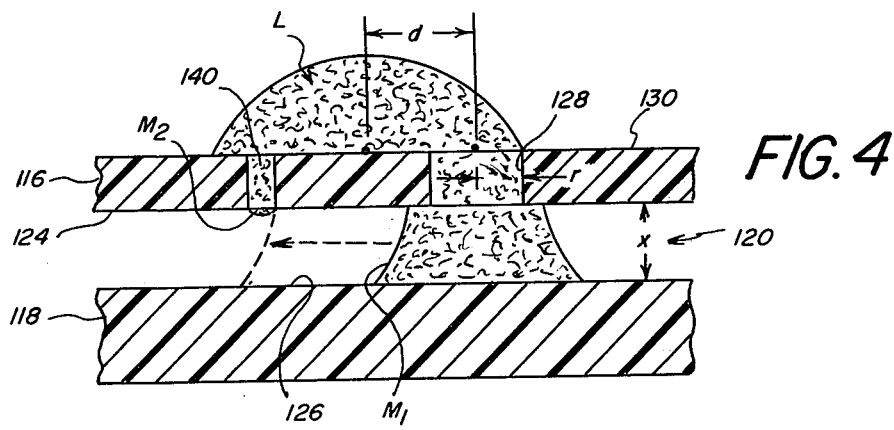
FIG. 4 is a section view taken generally along the line IV—IV of FIG. 3.

As illustrated in FIGS. 3 and 4, an improved liquid transport device 112 avoids the problem of noninitiation of flow into the device, noted above. Parts similar to those of FIG. 2 bear the same reference numeral to which the value 100 is added. Thus, device 112 comprises two members 116 and 118 spaced apart a distance "x" to provide a capillary transport passage 120, as is described for example in my aforesaid U.S. Pat. No. 4,233,029. An ingress aperture 128 is provided connecting exterior surface 130 to passage 120 in a manner similar to that described above. Preferably, the maximum flow-through diameter 2 r is less than about 3 mm.

In accordance with one aspect of the invention, aperture 128 is provided with at least one additional satellite aperture 140 to form a cluster of apertures as the ingress means. The satellite aperture 140, having a radius r', also is formed in member 116 extending from surface 130 to passage 120. As is described further hereinafter, aperture 140 assists in providing liquid ingress to passage 120.

Figure 5:
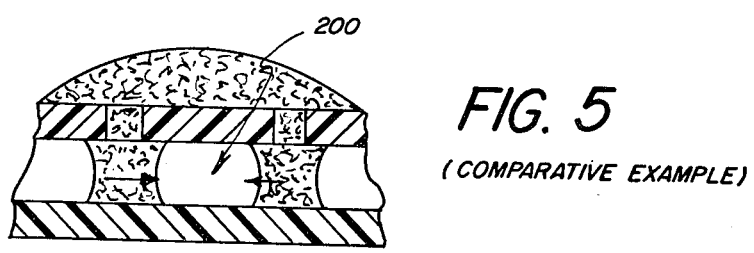
FIG. 5 is a fragmentary section view similar to that of FIG. 4, but illustrating a comparative example.

The cluster of apertures avoids the problems noted in the "Background". More specifically, the maximum flow-through dimension 2r' of any satellite aperture 140 is smaller than dimension 2r of aperture 128 and is smaller than that which will allow liquid within aperture 140 to contact surface 126, FIG. 4, and thus independently initiate flow within passage 120. Otherwise, as shown in the comparative example of FIG. 5, the independent flows occurring at apertures both of which initiate flow, could entrap air at pocket 200 when the two flows meet along irregularly shaped wavefronts. Such entrapped air tends to interfere with subsequent processing that is carried out within the device, for example, if it is used as an ion bridge as shown in FIG. 1.

The thickness of member 116 is selected in accordance with the wettability of the material used for member 116, such that liquid L penetrates through aperture 140 within a given time frame. Thus, the thickness is governed by the surface energetics of the material. If member 116 is polystyrene, for example, it should be no thicker than about 200 microns.

Thus, the dimensions of aperture 140 are selected so that the liquid within the aperture penetrates passage 120 sufficiently, and only sufficiently, to form a meniscus $M_2$, FIG. 4, such that, when the advancing meniscus $M_1$ arrives from aperture 128 as per the dotted arrow, meniscus $M_2$ coalesces with $M_1$. For such coalescence, meniscus $M_2$ is either generally convex, as shown, or generally concave, at surface 124. The particular shape will depend primarily upon the height of the head of liquid above exterior surface 130. For apertures 128 and 140 that are circular in flow-through shape, dimensions r and r' are radii. If apertures 128 and 140 are non-circular, dimensions r and r' are one-half the maximum flow-through dimensions.

A second reason for the dimension 2r' being less than dimension 2r of aperture 128 is that, as the dimension 2r' of aperture 140 approaches 2r of aperture 128, it becomes more and more difficult to insure that circumference $Z_3$ of aperture 140 falls within circumference $Z_2$ of the deposited liquid, as described hereinafter.

In accordance with another aspect of the invention, to prevent the intersection of the liquid meniscus with aperture 128, that aperture is sized to always be within the predictable contact area of the drop. To this end, the dimension "r" is selected to be no larger than the difference between the predicted radius R of the liquid deposit contact area, and the maximum expected error of displacement d of center $C_2$ compared to center $C_1$.

This relationship insures that the circumference $Z_2$ of quantity L, FIG. 3, will always encompass the circumference $Z_1$ of aperture 128.

Stated mathematically, the relationship is, $R=d+r$. As is readily apparent, this requires that the error d in displacement of the center $C_2$ from the aperture center $C_1$, always be less than radius R of the contact area of the deposited liquid. In apparatus tending to produce larger displacement errors d, radius r is decreased to avoid increasing radius R.

Therefore, r and $Z_1$ as shown in FIGS. 3 and 4 are maximum allowable values; and preferably aperture 128 has a radius and circumference, respectively, that are less than these.

The maximum displacement error is partially a function of the equipment used to deposit the liquid, and more specifically, of the tolerances inherent in the relative movement of the capillary transport device and that equipment, leading to the liquid-depositing step. The displacement error is also a function of tolerances within the transport device itself. If apertures 128 and 140 are not formed so as to be spaced an expected distance from a locating edge of the device, then those apertures are not going to be properly aligned with the apparatus used to deposit the liquid, even if the device is otherwise properly positioned.

The method of metering preferably proceeds as follows: Center $C_1$ of aperture 128, FIG. 3, represents the most likely, or ideal, location of the liquid L if metering occurs exactly as desired. Distance "d" represents the possible displacement error, arising from the aforementioned factors. To be certain that the larger aperture of the cluster is always encompassed by liquid L, the device 112 bearing that aperture is positioned relative to the metering apparatus so that such aperture is within circumference $Z_1$. That is, for an aperture 128 having a slightly smaller diameter than diameter 2r which is the "worst" case, $Z_1$ becomes a hypothetical circle within which the actual aperture 128 of a radius less than r, is located. Thus circumference $Z_1$ can be considered to be the circumference of the predetermined error range for the location of aperture 128 relative to center $C_1$, the ideal center of metering.

Thereafter, quantity L is deposited onto surface 130 so as to encompass aperture 128 and at least one of apertures 140.

Examples of useful values for $r \leq R - d$, in systems having a displacement error d of 0.125 mm and drop volume to 10 µl, are indicated below:

| Material Comprising Surface 130 | d | R | $r \leq (R-d)$ |
|---|---|---|---|
| Cellulose acetate | 0.125 mm | 2.1 mm | 1.9 mm |
| polystyrene | 0.125 mm | 1.9 mm | 1.7 mm |

The cluster is designed so that at least one satellite aperture 140 is also completely encompassed by the deposited liquid L. To achieve this result, the center $C_3$ of aperture 140 is preferably displaced from the center $C_1$ of aperture 128 in the direction of the expected displacement error. Furthermore, it is displaced by a distance δ, FIG. 3, that is no greater than that which will insure that its circumference $Z_3$ falls within and is encompassed by the contact area of deposited liquid L for the expected error of displacement. For example, for aperture 140 to be properly located when displacement is to the left of center $C_1$, FIG. 3, $\delta \leq R - r' = d$.

The exact range of values to be selected for r' in keeping with the aforementioned guidelines, varies depending upon several factors. To keep liquid in aperture 140 from independently contacting surface 126, the spacing x of the passage must be taken into account, as well as the height of the head of liquid created by the sesile drop L.

Assuming the preferred conditions of about 10 µl for the liquid, it can be shown that the head of liquid created by quantity L, FIG. 4, will always be less than the head necessary to force the liquid meniscus $M_2$ to form a hemispherical protuberance into passage 120. Therefore, under the preferred conditions of use, a hemispherical protuberance represents a worst case such that if r' of aperture 140 were to be equal to spacing x, aperture 140 would independently initiate flow within passage 120. To avoid this "worst case", r' of aperture 140 should be less than spacing x, or, for $0.05\ mm \leq x \leq 0.6$ mm as noted above for passage 20 of FIG. 2, the maximum that r' can be is a value just less than 0.05 mm up to a value just less than 0.6 mm, respectively.

An empirical test for the determination of the value of r' is, liquid L is deposited so as to circumscribe only the aperture 140 of interest. If flow is not initiated, then r' is sufficiently small.

It will be readily appreciated that the preferred values for r' are much less than the afore-noted maximums. Thus, for aperture 128 having a radius r of between about 0.75 mm to about 1.15 mm, and most preferably about 0.95 mm, aperture 140 preferably has a radius r' between about 0.05 mm and about 0.125 mm, most preferably about 0.075 mm.

When meniscus $M_1$ coalesces with meniscus $M_2$ as noted above, a second flow path is completed from liquid L on the surface, into the passage. It is this coalescence event which has been found to produce a reduction in the rate of traverse of passage 120 by the liquid. That is, the energy and time needed to bring about the coalescence reduces the rate of drainage into passage 120, and therefore also the flow rate within the passage. That this coalescence event should produce the reduction in drainage rate, was quite unexpected.

Most preferably, because the direction of the displacement error is usually unknown, more than one satellite aperture 140 is disposed, at approximately equal distances, around aperture 128, with aperture 128 located approximately in the center of the cluster. The spacing of the satellite apertures 140 is selected on the basis that the locus of center $C_2$ is to be found on or within a circle 150, shown as a dot-dash line, FIG. 3, having a radius d, the maximum error of displacement. Most preferably, apertures 140 are spaced so that, no matter where within circle 150 the center $C_2$ falls, the liquid contact area within circumference $Z_2$ will encompass at least one such satellite aperture. For example, four or five satellite apertures evenly spaced (about 90° or 72° respectively) around aperture 128 is a preferred cluster arrangement. The preferred distance δ of the center of each satellite aperture from $C_1$ is between about 1.25 mm and about 1.6 mm, and most preferably about 1.5 mm.

The use of one or more satellite holes has been found to produce several advantages. One advantage is that it acts to "pin down" the deposited quantity of liquid, preventing it from wandering over the deposit surface when device 112 is jarred or vibrated. Another advantage is that it produces more uniform and complete drainage or penetration of the liquid into the passage. A third is that it reduces the rate of flow.

Figure 6:
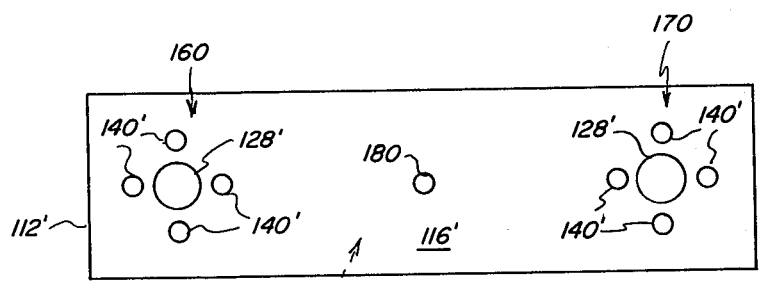
FIG. 6 is a plan view of an ion bridge incorporating the invention.

The afore-described improved access aperture means for conveying deposited liquid to an interior transport passage is useful for a variety of transport purposes. A preferred use is to provide an ion bridge for an ISE test element of the type shown in FIG. 1. FIG. 6 illustrates such an ion bridge 112', wherein two clusters 160 and 170 of apertures are provided, each with a center aperture 128' and four satellite apertures 140'. (Primes are added to reference numerals depicting features similar to those shown in the previously described embodiment.) One or more air vents 180 is preferably provided, generally centered between clusters 160 and 170, to allow the escape of entrapped air. In use, a drop of a sample liquid such as blood is deposited to encompass all of the aperture 128' and at least one satellite aperture 140' at one of the clusters 160 or 170, and at the other cluster, a drop of a reference liquid is similarly deposited. Preferably the depositions take place at about the same time. When the two drops meet by flowing under member 116' within passage 120', an electrical circuit is completed, allowing potentiometric measurements to be taken as is discribed in the aforesaid U.S. patent, using potentiometer 226 and contacts 224, FIG. 1.

The apertures in the lower member that lead to the ISE's are either generally aligned with apertures 128', or are offset as described in U.S. Pat. No. 4,271,119, issued on June 2, 1981.

The preferred embodiments are described herein in connection with liquid deposited as a drop. In addition, the invention is applicable to ingress apertures used for any deposited liquid, regardless of the shape or configuration the liquid assumes as it is being deposited. For example, the device is useful with liquid transferred to the device without assuming a drop shape.

The preferred embodiments also refer to the contact area formed by the deposited drop on the exterior surface as being generally the area of a circle having a predictable radius. Whether in fact a circle forms depends on whether the exterior surface for deposit is generally smooth, as in the preferred embodiments, or not. The invention is also applicable to non-circular contact areas, in which case "contact radius" is taken to mean the dimension of the contact area measured from the approximate center of that area to the liquid circumference, along the center line extending between the contact area center and the center of the ingress aperture, i.e., center $C_1$ in FIG. 3.

Still further, the preferred embodiments herein described refer to the use of the invention in an ion bridge for an ISE test element, wherein the ingress aperture is circular. In addition, the invention is applicable to an ingress aperture providing liquid access to a transport passage used for any other purpose. Furthermore, the invention is not restricted by the shape of the ingress apertures. For example, elliptical and polygonal shapes are useful also, particularly those having axisymmetry or a plane of symmetry.

EXAMPLES

The following examples further illustrate the invention.

EXAMPLES 1–2

A capillary passage was constructed using a nominally smooth sheet of polyethylene terephthalate as the bottom sheet, and a nominally smooth sheet of triacetate as the top sheet. The sheets were mounted so as to be spaced apart about 50 microns. Three such test elements were prepared, each with a different pattern of ingress apertures in the top sheet. In the Control, a single circular aperture was punched with a radius of about 0.76 mm. In Example 1, in addition to the aperture of the Control, four circular satellite apertures were punched 90° around the center aperture with radii of about 0.076 mm and centers 1.5 mm from the center of the main aperture. (See the clusters of FIG. 6.) In Example 2, the pattern of Example 1 was duplicated, except that 4 more satellite holes of identical dimensions were placed, evenly spaced, among the first 4 satellite apertures (45° apart). A drop of 10 µl of water was placed over the center aperture in each case, and over at least one other aperture in Examples 1 and 2, and the rate of drainage into the passage was timed. Drainage into the capillary passage was determined to have ended when there remained no head of liquid in the center aperture to continue driving the flow. The following Table sets forth the results:

TABLE

| Example | No. of Satellite Holes | Equivalent Flow-Through Diameter* | Drainage time into capillary passage (sec.) (±20%) |
| --- | --- | --- | --- |
| (Control) | 0 | 0.152 | 4 |
| 1 | 4 | 0.155 | 7 |
| 2 | 8 | 0.157 | 8 |

*= $(\Sigma \text{ Area of holes} \cdot 4/\pi)^{\frac{1}{2}}$

Thus, notwithstanding that the equivalent flow-through diameters increased slightly, the more satellite apertures that were present, the longer the drainage time. If any change would have been expected, it would have been the opposite. This delay in drainage time is advantageous as it provides a means for controlling flow in passages that tends to be too fast. For example, if flow occurs too rapidly from cluster 160 to cluster 170 in the device of FIG. 6, the liquid deposited at 160 might reach 170 before the liquid that is to be deposited at 170, enters the passage. Such mistiming could produce contamination.

The afore-mentioned delay is a feature of the invention that is useful whether or not the invention is applied to solve a displacement error problem. In such a use, the apertures have any shape, not just those with symmetry, and the larger aperture is as large as, or smaller than, those already described in the aforesaid U.S. Pat. No. 4,233,029.

The invention has been described in detail with particular reference to preferred embodiments thereof, but it will be understood that variations and modifications can be effected within the spirit and scope of the invention.

What is claimed is:

1. In a liquid transport device including an exterior surface adapted to receive a quantity of deposited liquid, wall means interior of said surface for transporting liquid within the device by capillary attraction along a passage, and access means for fluidly connecting said exterior surface and a portion of said passage so that liquid deposited on said exterior surface at said access means is transported to and along said passage,
the improvement wherein said access means comprises a cluster of at least two apertures extending from said exterior surface to said passage, only one of said apertures having a maximum flow-through dimension that is sufficiently large as to allow the liquid to independently initiate transport of liquid within said passage, and the others of said apertures having maximum flow-through dimensions that permit liquid to form a meniscus at a position that is capable of coalescing with liquid advancing within said passage, but not of independently initiating flow within said passage said apertures being positioned whereby liquid sample placed on the one of said apertures that allows independent transport will encompass at least one of the other apertures.

2. A device as defined in claim 1, wherein at least four of said other aPertures are disposed around said only one aperture.

3. A device as defined in claim 1, wherein at least said only one aperture has a circular flow-through shape.

4. A device as defined in claim 1, wherein all of said apertures have a circular flow-through shape.

5. A method for introducing a quantity of liquid into an interior capillary transport passage of a liquid transport device, the method comprising the steps of
(a) positioning such transport device having an exterior surface that includes a cluster of at least two apertures extending to said interior passage, only one of said apertures having a maximum flow-through dimension sufficiently large as to allow liquid to independently initiate transport in said passage when placed at said cluster, with said one larger aperture located within a predetermined error range measured from a desired metering position, the others of said apertures being sized to deliver to said passage a meniscus at a position that is capable of coalescing with liquid advancing within said passage, but not independently intiating flow within said passage and
(b) depositing such liquid onto said surface so as to encompass said one larger aperture and at least one other aperture of said cluster.

6. A method as defined in claim 5, wherein said liquid is deposited with a volume of about 10 $\mu$l onto said exterior surface to cover a contact area having a radius of about 2.1 mm, and wherein one-half of said maximum flow-through dimension of said one aperture is no larger than about 1.9 mm.

7. A method as defined in claim 5, wherein said liquid is deposited with a volume of about 10 $\mu$l onto said exterior surface to cover a contact area having a radius of about 1.9 mm, and wherein one-half of said maximum flow-through dimension of said one aperture is no larger than about 1.7 mm.

* * * * *